United States Patent [19]

Chowhan et al.

[11] Patent Number: 5,037,647

[45] Date of Patent: Aug. 6, 1991

[54] AQUEOUS ANTIMICROBIAL OPTHALMIC SOLUTIONS COMPRISED OF QUATERNARY AMMONIUM COMPOUND, CITRIC ACID, CITRATE AND SODIUM CHLORIDE

[75] Inventors: Masood A. Chowhan, Arlington; Danny O. Helton, Joshua; R. Gregg Harris, Fort Worth; Connie L. Luthy, Dallas, all of Tex.

[73] Assignee: Alcon Laboratories, Inc., Fort Worth, Tex.

[21] Appl. No.: 244,974

[22] Filed: Sep. 15, 1988

[51] Int. Cl.$^5$ ................... A61K 31/74; L11D 1/00
[52] U.S. Cl. ..................... 424/78; 514/839; 514/912; 252/174.23
[58] Field of Search ............. 514/839, 912; 424/78; 252/174.23

[56] References Cited

U.S. PATENT DOCUMENTS

| | | | |
|---|---|---|---|
| 4,407,791 | 10/1983 | Stark | 424/80 |
| 4,525,346 | 6/1985 | Stark | 424/80 |
| 4,734,222 | 3/1988 | Winterton et al. | 514/839 |

FOREIGN PATENT DOCUMENTS

| | | | |
|---|---|---|---|
| 180309 | 9/1985 | European Pat. Off. | |
| 8404681 | 12/1984 | PCT Int'l Appl. | 514/912 |

OTHER PUBLICATIONS

Plaut et al., "The Influence of Various Counter Ions on the Interaction of Chlorhexidine with the Hydrophilic Contact Lens Polymer, Poly(2-Hydroxyethyl Methacrylate)", *J. Pharm. Pharmacol.*, vol. 32, pp. 453-459 (1980).

*Primary Examiner*—Thurman K. Page
*Assistant Examiner*—Peter F. Kulkosky
*Attorney, Agent, or Firm*—James A. Arno; Sally S. Yeager

[57] ABSTRACT

Hypotonic contact lens care compositions containing a quaternary ammonium antimicrobial agent (e.g. Polyquad ®) and an anionic complexing agent (e.g. citrate) are disclosed. The compositions are useful in the disinfection of hydrophilic contact lenses, particularly Group IV lenses, and in the preservation of products for treating such lenses. Methods for use of the compositions for disinfecting and preserving are also disclosed.

2 Claims, No Drawings

AQUEOUS ANTIMICROBIAL OPTHALMIC SOLUTIONS COMPRISED OF QUATERNARY AMMONIUM COMPOUND, CITRIC ACID, CITRATE AND SODIUM CHLORIDE

BACKGROUND OF THE INVENTION

1. Field of the Invention

This invention relates to contact lens care compositions and methods. More particularly, this invention relates to solutions for treating and disinfecting soft contact lenses, particularly high water content ionic hydrophilic lenses.

2. Description of Related Art

Hydrophilic soft contact lenses, which are also referred to as hydrated gel lenses, are prepared by copolymerizing hydrophilic organic monomers having an olefinic double bond with a small amount of a cross-linking agent, usually having two polymerizable, olefinic double bonds. These lenses are usually based upon poly(hydroxyalkyl)methacrylates such as poly(hydroxyethyl)-methacrylate, cross-linked with, for example, ethylene glycol dimethacrylate, a hydroxyethyl dimethacrylate. The hydroxyl groups of the hydrated gel lenses render the lenses hydrophilic, i.e. they wet easily and absorb water. Other functional groups, such as carboxylic acid moieties from methacrylic acid copolymers, also contribute to lens hydrophilic character. With water absorption, the lenses also may take up chemicals dissolved in the water.

Hydrophilic contact lenses can be divided into four groups, namely, low and high water content nonionic lenses (Group I and Group II) and low and high water content ionic lenses (Group III and Group IV). The care of these types of hydrophilic lenses presents specific problems. However, the care of high water content ionic lenses (Group IV) can be particularly difficult due to the fact that many of the components of cleaning and disinfecting products have a tendency to bind to these lenses more than to other types of lenses.

Group IV lenses contain a relatively large number of exposed carboxylic acid groups, each of which is largely ionized, bearing a negative charge at physiologic pH. When contact lens care products containing compounds bearing positive charges are used with Group IV lenses, an ionic interaction can take place between the lenses and those components. Use of products containing such components can produce undesirable clinical symptoms in some persons, such as diffuse corneal staining and product intolerance.

Subsequent to the introduction of hydrophilic lenses, it was found that, those lenses, due to their gel structure and/or their affinity to adsorb or absorb materials, had a tendency to complex and concentrate most of the preservatives and disinfecting agents known at that time. The most common preservatives and disinfecting agents known at that time were sorbic acid, thimerosal, benzalkonium chloride and chlorhexidine. It was found that many of these preservatives and disinfecting agents become concentrated in the lenses to a sufficient degree that when the lens is placed in the aqueous environment of the eye, the preservatives or disinfectants are released from the lens and cause eye irritation. This problem was found to be particularly severe with positively charged preservatives or disinfecting components.

Isotonic aqueous solutions containing the polymeric quaternary ammonium chloride compound, Polyquad ® (registered trademark of Alcon Laboratories, Inc.) which is also known as Onamer ®M (registered trademark of Millmaster Onyx Group) has been used successfully to provide disinfecting and preservation properties to contact lens treating solutions, eye drop solutions and preserved saline solutions. The chemical name for Polyquad ® is α-4-[1-tris(2-hydroxyethyl)ammonium-2-butenyl]poly[1-dimethylammonium-2-butenyl]-ω-tris(2 hydroxyethyl)ammonium chloride. The salt has an average molecular weight generally in the range of from about 2,000 to about 30,000 and preferably in the range of about 3,000 to about 14,000. The compound has the general formula:

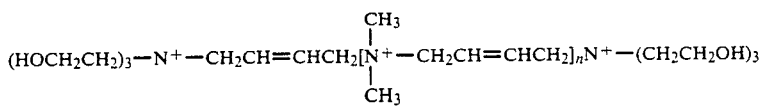

$$(n + 2)X^-$$

wherein X is a pharmaceutically acceptable anion, and in the case of Polyquad ® is chloride. The effective compound is a cation which is derived from the disassociation of a salt that has a pharmaceutically acceptable anion such as acetate, sorbate, or a halogen, preferably chloride or bromide.

Ophthalmic compositions containing Polyquad ® and methods for disinfecting contact lenses with solutions containing this polymer are disclosed in commonly assigned U.S. Pat. Nos. 4,525,346 and 4,407,791 both issued to Stark, June 25, 1985 and Oct. 4, 1983, respectively. These patents describe various types of ophthalmic products containing Polyquad ®, including products for treating contact lenses (e.g., disinfecting solutions) and products for more general ophthalmic use (e.g., comfort drops).

The compositions of the present invention comprise a polymeric quaternary ammonium compound, such as Polyquad ®, disclosed in the Stark patents referred to above. However, the compositions and methods described herein represent an improvement over those disclosed in the Stark patents because the present compositions and methods can be used to treat Group IV contact lenses. The compositions and methods disclosed in the Stark patents can also be used to treat Group IV lenses. However, it has been found that without the improvements described herein the compositions and methods of Stark may result in binding of Polyquad ® to the contact lens, at least with respect to some types of lenses and some types of lens care regimens. This binding problem has stood in the way of commercial use of the Stark compositions and methods in conjunction with Group IV lenses. The problem has been solved by the present invention.

SUMMARY OF THE INVENTION

The compositions of the present invention comprise a polymeric quaternary ammonium compound such as Polyquad ® and an anionic complexing agent which prevents the quaternary ammonium compound from associating, or binding, with the negatively charged moieties of soft contact lenses, particularly Group IV lenses. In particular, citrate ions are used to complex with Polyquad ®. Citrate functions to complex Polyquad ®, but, Polyquad ® is not complexed so tightly that its antimicrobial effectiveness is significantly reduced. In addition it is also necessary that the tonicity of the present compositions be reduced so that the solutions are slightly hypotonic. This reduction in tonicity is required in order to maintain adequate antimicrobial activity. Thus, the present invention is based on the discovery that concurrent inclusion of an anion, such as citrate, and lowering of tonicity to increase antimicrobial activity, results in contact lens care solutions which can be used with all types of hydrophilic contact lenses, including Group IV lenses.

The compositions of the present invention can be used as a cold, chemical disinfecting and storage solution for all types of soft contact lenses, particularly Group IV lenses. The compositions can also be used as a preserved saline solution for rinsing and as an in-the-eye drop to rehydrate lenses.

DETAILED DESCRIPTION OF THE PREFERRED EMBODIMENT

The hypotonic contact lens care compositions of the present invention comprise a quaternary ammonium antimicrobial agent and an anionic complexing agent capable of binding with the quaternary ammonium agent to an extent such that binding of the quaternary ammonium agent to Class IV contact lenses is substantially prevented. The quaternary ammonium antimicrobial agents utilized in the present invention must be effective in eliminating microorganisms from contact lenses and in preventing contact lens care products from being contaminated by microorganisms, and must be safe for use in disinfecting contact lenses and preserving contact lens care products. Specific examples of quaternary ammonium antimicrobial agents which may find use in the present invention include: monomeric and polymeric biguanides, such as chlorhexidine and the polyhexamethylene biguanides disclosed in European patent publication EP 180,309 AI, respectively; benzalkonium chloride; and tris(2-hydroxyethyl)-tallow ammonium chloride. The preferred quaternary ammonium antimicrobial agents are polymeric compounds of the following formula:

The compositions of the present invention also include an anionic complexing agent. The anion used as a complexing agent functions to bind Polyquad ® in much the same way that Polyquad ® binds with hydrophilic lenses, particularly Group IV lenses thereby reducing the quaternary ammonium antimicrobial agent binding with the lenses. The complexing agents which may be used include: citrate, phosphate, malonate, maleate, acetate, edetate, ethanol diglycinate, diethanolglycinate and polystyrene sulfonate, or combinations thereof. A complexing agent comprising citrate is preferred because it serves to complex with Polyquad ® to the extent that Polyquad ® adhesion to hydrophilic lenses is reduced to clinically acceptable levels, but complexation is not so strong that the antimicrobial efficacy is reduced to clinically unacceptable levels. In addition, in order to achieve optimum reduction of uptake by the lenses without compromising efficacy it is also necessary to reduce the tonicity of the compositions so that the solutions are slightly hypotonic.

According to the preferred embodiment of the present invention, citrate ions are used to prevent absorption or adsorption of Polyquad ® molecules on hydrophilic lenses, particularly Group IV lenses. The concentration of citrate ions and the other ions of the compositions is such that Polyquad ® is complexed with the citrate ions and substantially prevented from associating with hydrophilic lenses without sacrificing the disinfecting or preservation properties of Polyquad ®. Additionally the compositions of the present invention use a citrate buffer system. Thus, there must be enough citrate present to function both as an anionic complexing agent and as an ion of the citrate buffer system which functions to keep the pH of the compositions at physiologically acceptable levels. This concentration of citrate ions can be between about 0.001 and 1.5 weight percent (wt. %), preferably between about 0.01 and 1.0 wt. %, most preferably 0.6 wt. %.

As previously stated, in addition to the inclusion of an anionic complexing agent, such as citrate, to substantially prevent Polyquad ® from complexing with hydrophilic lenses, it has also been found that the tonicity of the compositions is important. Compositions of the present invention are made hypotonic by adjusting the sodium chloride concentration from proportion of sodium ions, like the anionic complexing agent citrate, influences the binding of Polyquad ® to lenses. Sodium

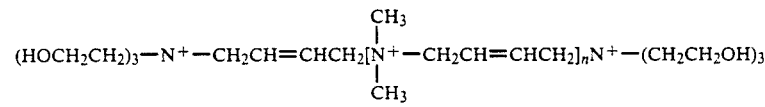

(n + 2)X⁻ wherein X is a pharmaceutically acceptable anion, such as chloride, bromide, acetate, or sorbate. The most preferred polymers are those wherein X is chloride; as indicated above, the chloride salts of these polymers are also known as Polyquad ® and Onamer ®M.

The salts from the above identified polymeric quaternary ammonium compounds have a molecular weight of about 2,000 to 30,000, preferably about 3,000 to 14,000, most preferably 4,000 to 7,000. The quaternary ammonium salt is present in compositions of the present composition at concentrations of about 0.00001 to 3.0 weight percent (wt. %), preferably 0.0001 to 0.1 wt. %, most preferably about 0.0005 to 0.01 wt. %.

ions are positively charged ions which interact with the negatively charged moieties of hydrophilic lenses and with the negatively charged target molecules in microbes' walls or membranes. When the sodium ion concentration is reduced, there are fewer positively charged components competing for binding or complexation with both the lenses and the microbes. Therefore, reduction of sodium ions, although allowing for increased binding of Polyquad ® to hydrophilic lenses, also allows for increased binding of Polyquad ® with microbes. Thus, the concentration of sodium chloride is adjusted so as to make the solutions slightly hypotonic thereby increasing the antimicrobial activity of Polyquad ®, while at the same time an anionic complexing agent is added to prevent excessive binding of Polyquad ® to the lenses. The concentration of sodium chloride present in the compositions disclosed herein is such that the compositions are made hypotonic with an osmolality between about 210 and 240 mOsm/kg.

The preferred composition of the present invention comprises the following components at the indicated concentrations represented as weight/volume percent (wt. %): Polyquad ®, 0.001 wt. % (plus 10 wt. % excess), citric acid monohydrate, 0.021 wt. %, sodium citrate dihydrate, 0.56 wt. %, edetate disodium, 0.05 wt. %, and sodium chloride at 0.516 wt. %. The composition is adjusted to a pH of about 6.5 to 7.5, preferably 7.0, using hydrochloric acid or sodium hydroxide. The osmolality of the composition is about 210 to 240 mOsm/kg, preferably 220 mOsm/kg.

The compositions disclosed herein can include other components. For example anionic surfactants can be included to contribute to the prevention of Polyquad ® binding to hydrophilic lenses and to enhance antimicrobial activity of the compositions. Nonionic surfactants can be added to enhance antimicrobial activity, but unlike anionic surfactants, would not contribute to the complexing of Polyquad ®.

The following example representative of a composition of the invention and should not be construed as limiting.

EXAMPLE I

| Preserved Saline Solution | Wt. % |
|---|---|
| Polyquad$^R$ | 0.001 + 10% excess |
| Sodium Chloride | 0.48 |
| Disodium edetate | 0.05 |
| Citric acid monohydrate | 0.021 |
| Sodium citrate dihydrate | 0.56 |
| Purified Water | q.s. |

Procedure

A 45 liter carboy was filled with about 40 liters of purified water and the sodium citrate dihydrate, citric acid monohydrate, disodium edetate, sodium chloride and Polyquad ® in the concentrations indicated in the table above. The components were allowed to dissolve by stirring with a mixer. Purified water was added to bring the solution to almost 100%. The pH was recorded at 6.323 and adjusted to 7.0 with NaOH. Purified water was added to bring the solution to 100%. The solution was stirred and a pH reading of 7.011 was taken. The solution was then filtered into sterile bottles and capped.

The invention in its broader aspects is not limited to the specific details shown and described. Departures may be made from such details within the scope of the accompanying claims without departing from the principles of the invention and without sacrificing its advantages.

We claim:

1. A hypotonic contact lens composition, comprising: 0.001 wt. % of a quaternary ammonium compound having an average molecular weight in the range of about 4,000 to 7,000, said compound having the formula

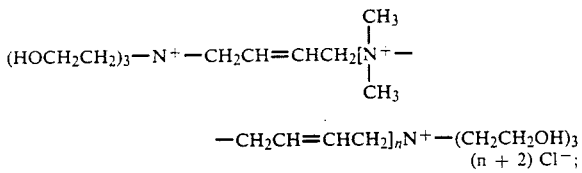

about 0.021 wt. % citric acid monohydrate, 0.56 wt. % sodium citrate dihydrate, 0.05 wt. % edetate disodium, 0.516 wt. % sodium chloride; the composition having an osmolality of about 220 to 230 mOsm/kg.

2. A method of disinfecting a hydrophilic contact lens which comprises applying the composition of claim 1 to the lens.

* * * * *